US00PP16304P2

(12) United States Plant Patent
Danziger

(10) Patent No.: US PP16,304 P2
(45) Date of Patent: Mar. 7, 2006

(54) ***TORENIA* PLANT NAMED 'DANTORWHITE'**

(50) Latin Name: ***Torenia* sp.**
Varietal Denomination: Dantorwhite

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 168 days.

(21) Appl. No.: 10/929,421

(22) Filed: Aug. 31, 2004

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,105 P2 * 9/2001 Miyazaki ..... Plt./263
2004/0128722 P1 * 7/2004 Iwaki ..... Plt./263

OTHER PUBLICATIONS

UPOV ROM GTITM Computer Database, GTI Jouve Retrieval Software 2004/06 Citation for 'Dantorwhite'.*

* cited by examiner

*Primary Examiner*—Anne Marie Grunberg
*Assistant Examiner*—W. C. Haas
(74) *Attorney, Agent, or Firm*—Foley & Lardner, LLP

(57) ABSTRACT

A new and distinct *Torenia* plant named 'Dantorwhite' particularly characterized by having shiny green foliage, dotted with plenty of delicate, cup shaped flowers in shades of white with a yellow throat; bush cascading, vigorous, compact rounded growth, densely branched; early flowering, flowers all year round in moderate climate; suitable for use as an annual for hanging pots outdoors under partial shade; and good weather tolerance with preferred temperature range of 15–25° C.

2 Drawing Sheets

Botanical designation: *Torenia* sp.
Variety denomination: 'Dantorwhite'.

BACKGROUND OF THE INVENTION

The present invention relates to a new and distinct cultivar of *Torenia* plant of the Scrophulariaceae family, hereinafter referred to by the cultivar name 'Dantorwhite'.

The new cultivar originated in a controlled breeding program in Moshav Mishmar Hashiva, Israel. 'Dantorwhite' was discovered and selected by the inventor, Gabriel Danziger, as an induced shoot mutation on a single flowering plant of the cultivar 'Rose Moon', grown in a controlled, cultivated environment in Moshav Mishmar Hashiva, Israel.

'Dantorwhite' is an induced mutant of the cultivar *Torenia* 'Rose Moon' (unpatented), selected in a cultivated environment in Moshav Mishmar Hashiva, Israel. The mutation arose by radiation, as a side shoot, and was stabilized by removing the shoot as a cutting from the mutated sector of the treated parent plant.

Asexual reproduction of the new cultivar by soft tip cuttings was first performed in September, 2002 in Moshav Mishmar Hashiva, Israel and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Dantorwhite' which in combination distinguish this *Torenia* as a new and distinct cultivar:

1. Shiny green foliage, dotted with plenty of delicate, cup shaped flowers in shades of white with a yellow throat;
2. Bush cascading, vigorous, compact rounded growth, densely branched;
3. Early flowering, flowers all year round in moderate climate;
4. Suitable for use as an annual for hanging pots outdoors under partial shade; and
5. Good weather tolerance with preferred temperature range of 15–25° C.

Of the many commercial cultivars known to the present inventor, the most similar in comparison to 'Dantorwhite' is the parental cultivar *Torenia* 'Rose Moon'. Table 1 shows a comparison between 'Dantorwhite' and 'Rose Moon'.

TABLE 1

| Characteristic | 'Dantorwhite' | *Torenia* 'Rose Moon' |
|---|---|---|
| Flower color | White and Yellow | Light Red-Purple |
| Flower size (inch) (width by length) | 1.2 × 1.4 | 1.2 × 1.4 |
| Growth habit | Bush cascading | Bush cascading |
| Flowering time | 8 weeks from planting | 8 weeks from planting |

'Dantorwhite' has not been observed under all possible environmental conditions. The phenotype of the new cultivar may vary with variations in environment such as temperature, light intensity, and day length without any change in the genotype of the plant. The following observations, measurements and values describe the new cultivar as grown in Moshav Mishmar Hashiva, Israel under conditions, which closely approximate those generally used in commercial practice.

BRIEF DESCRIPTION OF THE DRAWING

The accompanying color photographs show typical flower and foliage characteristics of 'Dantorwhite', with the colors being as true as possible with illustrations of this type. The accompanying photographic illustrations show:

The first drawing shows: a flowering plant of 'Dantorwhite' in its entirety.

The second drawing shows a close up of 'Dantorwhite'.

DETAILED BOTANICAL DESCRIPTION

The following observations, measurements and values describe the new cultivar as grown in Moshav Mishmar Hashiva, Israel under conditions, which closely approximate those generally used in commercial practice. For use as a pot plant, optimal growth conditions include grown outdoors in moderate climate, and indoors during winter. Irrigation and fertilization on a regular basis. The plant is usually grown in full sunlight, but partial shade is required in mid summer. Plants are fully grown in three months from planting a cutting, and blooms all year-round in moderate climate.

Color references are made to The Royal Horticultural Society Colour Chart (R.H.S.), except where general colors of ordinary significance are used. Color values were taken under daylight conditions at approximately noon in Moshav Mishmar Hashiva, Israel in the September 2002 season. The age of the plant described is three months.

Propagation: Tissue culture propagation of young, in vitro plantlets and soft tip cuttings.

Plant:

*Form.*—Bush cascading.

*Growth habit.*—Rounded and compact.

*Height.*—6 inches.

*Spreading area.*—20 inches across.

*Blooming period.*—All year round in moderate climate.

*Cold tolerance.*—Frost tender, plants may be damaged by temp. below 5° C.

*Vigor.*—Plants are fully grown in 3 months from planting a cutting.

Stem:

*Color.*—Yellow-Green 144-A.

*Diameter.*—0.1 inch.

*Length.*—25 cm maximum length.

*Pubescence.*—Minimal; the stem is quadrangular; hairs are on the edges especially.

*Length of internodes.*—1.5 inches.

*Branching.*—About 20 main branches from the base that split into secondary and tertiary branches.

Foliage:

*Overall shape.*—Deltoid. Base: Cordate. Tip: Acuminate. Margin: Serrate.

*Color.*—Center color of leaf: Yellow-Green 147-A. Upper side: Yellow-Green 147-A. Under side: Yellow-Green 147-B.

*Size of leaf.*—Width: 1.0 inch. Length: 1.5 inches. Petioles: Length, about 1.0 cm; Diameter, about 0.15 cm, Yellow-Green 144-A. Leaf texture: Convex. Venation: Not prominent.

Flowers:

*Blooming period.*—All year round in moderate climate.

*Flowering stem.*—Flowers appear along the growing stems.

*Orientation at opening.*—Slantly upward.

*Type.*—Single.

*Shape.*—Funnel form.

*Petals.*—Size: 1.2 inches (width)×1.4 inches (length). Shape: Corolla tube cylindrical or often broadened above, 2-lipped, the upper lip faintly 2-lobed, the lower lip 3-lobed. Color: The corolla is white with a yellow blotch at the lower lip and a yellow throat. Mature and immature upper side: RHS 155 C, and RHS 1 A. Mature and immature under side: RHS 155 C, and RHS 3 C. Mature and immature margin: RHS 155 C. Throat: RHS 1 A.

*Peduncle.*—Length: 0.3 inch. Diameter: About 0.2 cm. Texture: Smooth. Color: Yellow-Green 144-A.

*Bud.*—Shape: Oblong cylindrical ellipsoid 5 winged. Size: Length: 1.2 cm. Diameter: 0.3 inch. Color: RHS 4 D.

Reproductive organs:

*Stamen.*—2 pairs, white RHS 155 C.

*Style.*—White RHS 155 C in color; 1.7 cm in length.

*Anther.*—White RHS 155 C in color; about 0.3 cm in length.

*Filament.*—White RHS 155 C.

*Ovaries.*—1, green RHS 143-B.

*Pollen color.*—RHS 155 C.

*Pistil length.*—About 2.2 cm.

*Stigma.*—Shape: 2 lobed. Color: RHS 76 B.

Seed/fruit: None.

Pest/disease resistance and/or susceptibility: A standard preventative spray program is sufficient as no susceptibility was observed.

I claim:

1. A new and distinct *Torenia* plant named 'Dantorwhite' as illustrated and described herein.

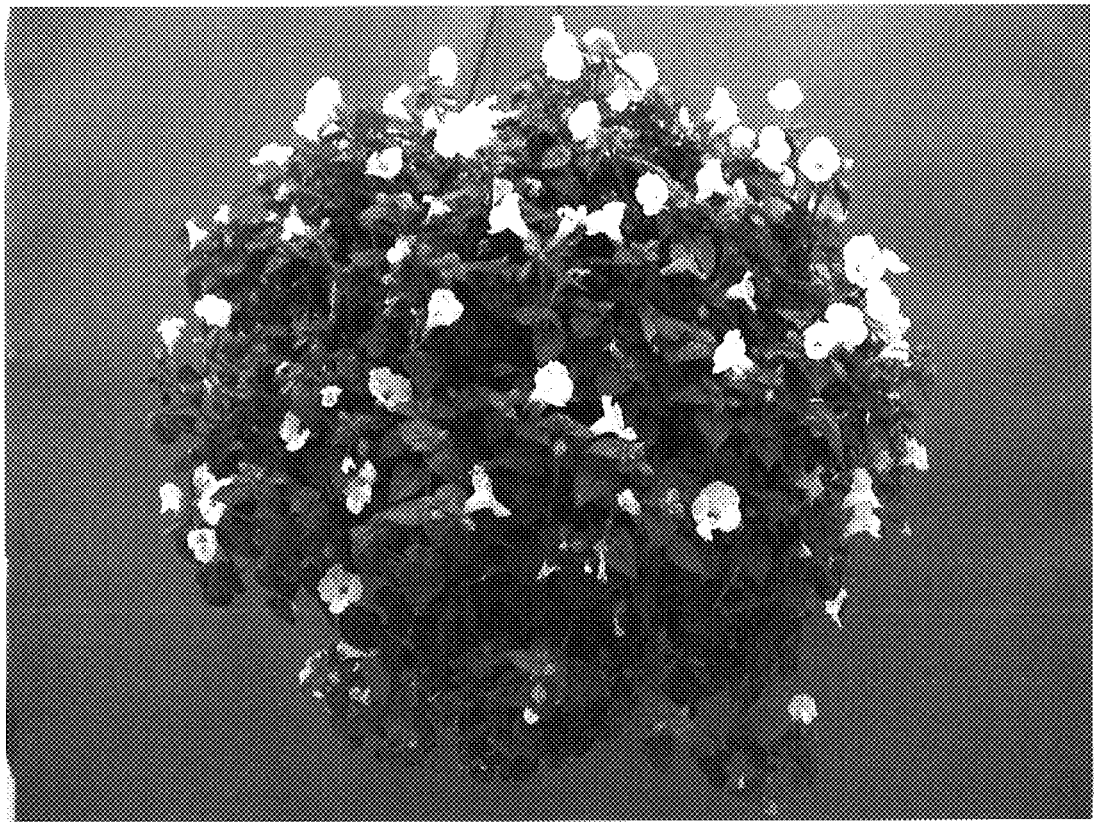

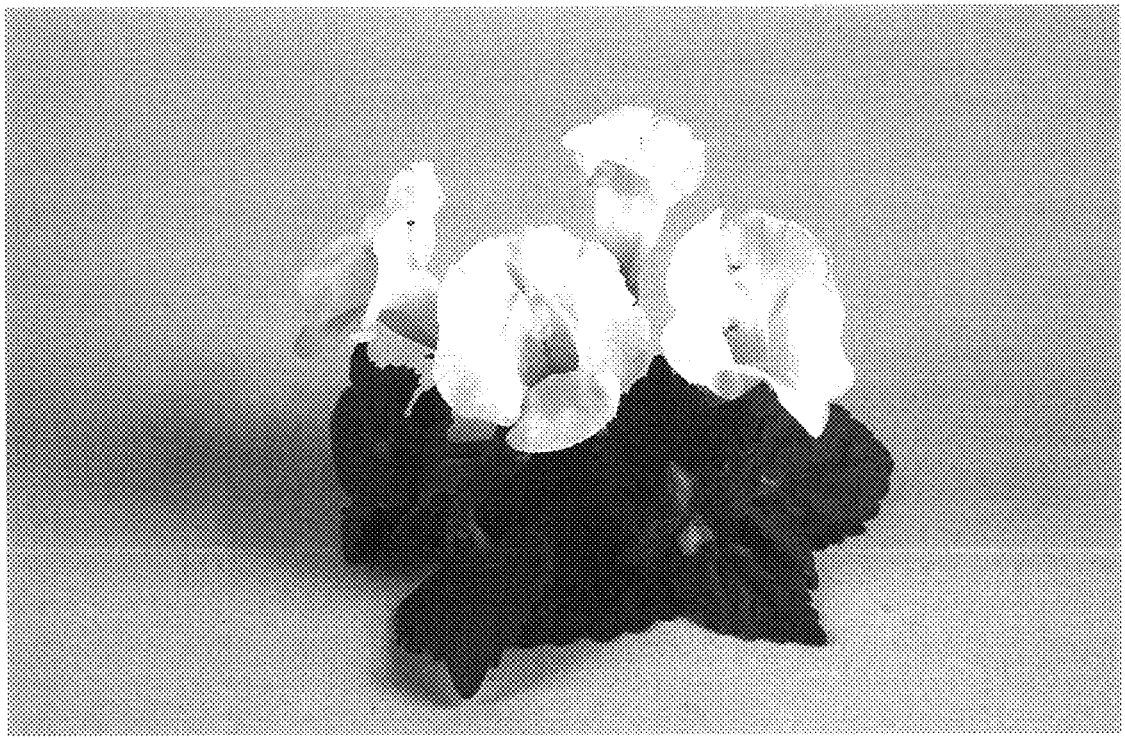

* * * * *